(12) United States Patent
Rosen (10) Patent No.: US 9,943,613 B2
(45) Date of Patent: Apr. 17, 2018

(54) DAB-4 LINKED NITROXIDE CITRATE, USEFUL AS MRI CONTRAST AGENT

(71) Applicant: Gerald M. Rosen, Rockville, MD (US)

(72) Inventor: Gerald M. Rosen, Rockville, MD (US)

( * ) Notice: Subject to any disclaimer, the term of this patent is extended or adjusted under 35 U.S.C. 154(b) by 115 days.

(21) Appl. No.: 14/437,637

(22) PCT Filed: Oct. 21, 2013

(86) PCT No.: PCT/US2013/065875
§ 371 (c)(1),
(2) Date: Apr. 22, 2015

(87) PCT Pub. No.: WO2014/066230
PCT Pub. Date: May 1, 2014

(65) Prior Publication Data
US 2015/0273087 A1 Oct. 1, 2015

Related U.S. Application Data

(60) Provisional application No. 61/717,248, filed on Oct. 23, 2012.

(51) Int. Cl.
*A61K 49/20* (2006.01)
*A61B 5/00* (2006.01)
*G01R 33/56* (2006.01)
*A61B 5/055* (2006.01)

(52) U.S. Cl.
CPC ............ *A61K 49/20* (2013.01); *A61B 5/055* (2013.01); *A61B 5/4514* (2013.01); *A61B 5/4528* (2013.01); *G01R 33/5601* (2013.01); *A61B 5/4576* (2013.01); *A61B 5/4585* (2013.01); *A61B 2503/08* (2013.01); *A61B 2576/02* (2013.01)

(58) Field of Classification Search
None
See application file for complete search history.

(56) References Cited

U.S. PATENT DOCUMENTS

| | | |
|---|---|---|
| 5,104,641 A | 4/1992 | Rosen |
| 5,567,411 A | 10/1996 | Keana et al. |
| 6,991,778 B2 | 1/2006 | Rosen |
| 8,114,393 B2 | 2/2012 | Deluca et al. |
| 2003/0215390 A1 | 11/2003 | Rosen |

FOREIGN PATENT DOCUMENTS

WO 01/41640 A1 6/2001

OTHER PUBLICATIONS

Shukla et al. Effects of PAMAM dendrimer salt solutions on protein stability. 2011 J. Phys. Chem. Lett. 2: 1782-1788. Published online Jul. 1, 2011.*
International Search Report dated Jan. 28, 2014 issued in corresponding PCT/US2013/065875 application (pp. 1-2).
C.S. Winalski et al., "Magnetic Resonance Relaxivity of Dendrimer-Linked Nitroxides", Magnetic Resonance in Medicine, vol. 48 (2002) pp. 965-972.
Winalski et al., "Targeted Dendrimer-based Contrast Agent for Articular Cartilage Assessment by MR Imaging", Osteoarthritis and Cartilage (2008) 16, pp. 815-822.
Maiti et al., "Structure of PAMAM Dendrimers: Generations 1 through 11", Macromolecules 2004, 37, pp. 6236-6254.
Winalski et al., "Magnetic Resonance Relaxivity of Dendrimer-Linked Nitroxides", Magnetic Resonance in Medicine 48: pp. 965-972 (2002).
Midura et al., "In vitro Toxicity in Long-term Cell Culture of MR Contrast Agents Targeted to Cartilage Evaluation", Osteoarthritis and Cartilage 22 (2014) pp. 1337-1345.
Drug Solubility: How to Measure It, How to Improve It, Theme Editors: J. Dressman, C. Reppas, A.T.M. Serajuddin, Advanced Drug Delivery Reviews 59 (2007) pp. 603-616.

* cited by examiner

*Primary Examiner* — Michael G Hartley
*Assistant Examiner* — Jennifer Lamberski
(74) *Attorney, Agent, or Firm* — Millen, White, Zelano, Branigan, P.C.

(57) ABSTRACT

A method of imaging a joint of a subject comprises administering to the subject an amount of a salt of DAB-4 linked nitroxide citrate effective to enhance an MRI image of the joint and taking an MRI image of said joint.

8 Claims, 11 Drawing Sheets

DAB-4 LINKED NITROXIDE CITRATE, USEFUL AS MRI CONTRAST AGENT

Osteoarthritis is the most common joint disease and is present in the majority of people who are over 60 years old (D. T. Felson, Epidemiology of the rheumatic diseases, In, *Arthritis and Allied Conditions: A Textbook of Rheumatology*, 13th edition, (W. J. Koopman, ed.), Williams and Wilkins, Baltimore, 1997). Osteoarthritis can involve almost any joint, but most commonly involves distal and proximal interphalangeal joints in the hands, hips, knees, and cervical and lumbosacral spine. Clinical features of osteoarthritis include pain in the involved joints which is aggravated by activity and relieved by rest, stiffness after periods of immobility, joint enlargement, and ultimately, functional impairment with joint instability and loss of motion.

Articular cartilage is a critical component of efficient, painless joint function. Osteoarthritis is characterized by progressive loss of articular cartilage. Recent advances in the understanding of the pathogenesis of osteoarthritis suggest that it is possible to develop drugs that will be able to reverse pre-existing abnormalities in articular cartilage or prevent their progression, if therapy is started early during the course of the disease. This is the theory behind the development of Rofecoxide by Merck. As a result, there is a tremendous need for a non-invasive technique that can accurately measure early cartilage degradation and the progression of those abnormalities.

To date, radiography has been limited in its ability to accurately evaluate cartilage disorders, because it is limited to measuring the joint space width—the distance between the bones (J. C. Buckland-Wright, D. G. Macfarlane, J. A. Lynch, M. K. Jasani, C. R. Bradshaw, Joint space width measures cartilage thickness in osteoarthritis of the knee: high resolution plain films and double contrast macroradiographic investigation. *Ann. Rheum. Dis.* 54: 263-268, 1995); (J. C. Buckland-Wright, D. G. Macfarlane, S. A. Williams, R. J. Ward. Accuracy and precision of joint space width measurements in standard and macroradiographs of osteoarthritic knees. *Ann. Rheum. Dis.* 54: 872-880, 1995). Cartilage cannot be imaged directly by this method. The osseous abnormalities (such as osteophyte formation) that eventually develop with osteoarthritis are not sensitive indicators of early disease, nor are they reliable measures of disease progression (M. W. Spring, J. C. Buckland-Wright. Contrast medium imbibition in osteoarthritic cartilage. *Br. J. Radiol*, 63: 821-825, 1990). Over the past several years, a great deal of attention has focused on the use of advanced cross-sectional imaging techniques, such as magnetic resonance (MR) imaging for the assessment of abnormalities in articular cartilage. Numerous MR sequences and techniques have been evaluated. Unfortunately, these studies have yielded variable, contradictory and often disappointing results. As a consequence, there is no universally accepted "best sequence or technique" for accurate MR imaging of articular cartilage. Inclusion of intraarticular injection of the contrast agent gadolinium (Gd)-DTPA has shown promise for the evaluation of proteoglycan status and cartilage morphology. However, the images must be post-processed with the calculation of T1 measurements, limiting the acceptance of the technique.

This invention describes a diagnostic method taking advantage of a particular dendrimer-linked nitroxide, as a selective contrast agent to improve the MR evaluation of cartilage status in humans; and/or to diagnose the presence of the above-described osteoarthritis and/or related diseases and conditions, e.g., those involving disorders of or loss of articular cartilage, e.g., in any joint, including those mentioned above. Specifically, a dendrimer-linked nitroxide with four terminal nitroxide groups has been synthesized that exhibits high relaxivity, thereby allowing MR contrast enhancement at clinically relevant concentrations (e.g., those typically used for Gd-DTPA). This dendrimer-linked nitroxide, when injected into the joint directly, exhibits high in vivo stability, low toxicity and very high efficacy, diffusing into cartilage at a rapid rate, verifying its unexpectedly good properties as an MR contrast agent to accurately evaluate cartilage status in humans and achieve the other effects described above and below.

Nitroxyl functionalized dendrimers are known. See, e.g., A. W. Bosmann et al., "Five Generations of Nitroxyl-Functionalized Dendrimers," Macromolecules, American Chemical Society, Easton, US, vol. 30, No. 12, pp. 3606-3611, Jun. 16, 1997.

Bosmann's dendrimers are poly (propylene imine) dendrimers (DAB-dendr-$(NH_2)_n$; where n=2, 4, 8, 16, 32 ... ) functionalized with 3-carboxy-2,2,5,5-tetramethyl-1-pyrrolidinyloxy(3-carboxy-PROXYL) radicals. Herein, such compounds are abbreviated as DAB-4 linked nitroxide (wherein n in such dendrimer is 4, DAB-dendrimer-(NH-3-CO-PROXYL)$_4$), DAB-8 linked nitroxide (wherein n is 8, DAB-dendrimer-(NH-3-CO-PROXYL)$_8$). This invention relates to the use of one set of these dendrimers, i.e., salts of DAB-4 linked nitroxide as MRI contrast agents for imaging joints.

Thus, it is an object of this invention to provide a method of MRI imaging of joints in a subject. It is also an object to provide an MRI method of evaluating cartilage status in joints. It is further an object to provide such methods achieving the characteristics outlined above and below.

The present invention provides such a method of imaging a joint by MR-imaging ("MRI imaging") comprising imaging a joint of a subject (e.g., an animal, e.g., domestic animals (cats, dogs, etc.), humans, etc.) whose joint tissue contains a DAB-4 linked nitroxide citrate salt in an amount effective for MRI image enhancement. A preferred method comprises administering the salt of DAB-4 linked nitroxide to a subject in need of MRI imaging of a joint and then MRI imaging such joint. In another aspect, the method comprises MRI imaging of a joint of a subject to whom a DAB-4 linked nitroxide citrate salt has been administered. In yet other aspects, such methods comprise evaluating cartilage status in joints, e.g., articular cartilage assessment.

The high usefulness of DAB-4 linked nitroxide citrate salt for enhancing MRI images of joints is unexpected in view of the prior art. In discussing the use of DAB-dendr-$(NH_2)_n$ dendrimers functionalized with 3-carboxy-PROXYL as MRI contrast agents for imaging joints, U.S. Pat. No. 6,991,778 requires that there be at least six nitroxyl-functionalized 3-carboxy-PROXYL groups in such dendrimers (DAB-6), thereby excluding DAB-4 linked nitroxide salts of this invention from such use. However, surprisingly and unanticipated, despite their lower relaxivity than such dendrimers containing more nitroxyl-groups (e.g., Table 1 of '778), DAB-4 linked nitroxide citrate salt have overall characteristics overcoming this clear prior art prejudice, as well as that of Winalski et al., Osteoarthritis and Cartilage (2008) 16, 815-822, and making them unexpectedly useful as MRI contrast agents for joints, e.g., especially because of rapid diffusion into joint tissue, yielding high quality images after only relatively short times after injection.

DAB-4 linked nitroxide and its salts can be prepared as presented in the examples below or as described in Bosmann et at above. Its salts, as well, are conventionally preparable, e.g., analogously to the examples below, e.g., by simply mixing the respective preferably organic acid with DAB-4 linked nitroxide. Suitable salts other than the citrates which are operable are pharmaceutically acceptable salts, e.g., such salts prepared by conventional reaction with acids known for use in the pharmaceutical field. These include, but are not limited to, organic acids which may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid (for the citrates of the invention), aspartic acid, ascorbic acid, glutamic acid, anthranilic acid, benzoic acid, cinnamic acid, mandelic acid, embonic (pamoic) acid, phenylacetic acid, methanesulfonic acid, ethanesulfonic acid, p-toluenesulfonic acid, salicyclic acid and the like.

A particularly preferred salt is DAB-4 linked nitroxide citrate, e.g., that formed with a 1:1 molar mixture of DAB-4 linked nitroxide and citric acid. Other molar ratios of acid and DAB-4 linked nitroxide can also be used, e.g., 2:1 to 1:2, etc., in dependence, e.g., on the number of COOH groups or other acid moieties in the acid.

The term "joint" as used herein embraces any joint as the term embraces in the medical field, including joints of the fingers, toes, feet, hands, wrists, ankles, knees, elbows, neck, shoulders, back, hips, etc. Because the joints most frequently examined to evaluate their morphology are the knee and shoulder joints, these are a preferred aspect of the method of this invention.

The term "animal" or "subject" preferably means a human being. However, other animals, ordinarily mammals, and particularly valuable domestic mammals, such as dogs, cats, race horses, etc., are also embraced by the term.

The term "pharmaceutically acceptable carrier" is entirely conventional and includes all well-known carriers for conventional MRI contrast agents used to image joints, e.g., PBS conventionally sterilized for injection, etc.

The dendrimer-linked nitroxide is ordinarily injected as a solution in a non-toxic injectable pharmacologically acceptable sterile aqueous vehicle, e.g., phosphate buffered saline (PBS) solution. The aqueous vehicle can also contain conventional amounts of other ingredients conventionally present in solutions which are injected into a joint, e.g., local anaesthetic, anti-inflammatory agents, e.g., cortisone, antibiotics, stabilizing agents, suspending agents.

The concentration of the DAB-4 linked nitroxide citrate salt in a phosphate buffered saline solution is usually from about 1 to 10 millimolar (mM), preferably from about 1 to 5 mM.

The amount of DAB-4 linked nitroxide citrate salt injected into the joint, as is well known, is influenced by the volume of the joint void, the concentration of the DAB-4 linked nitroxide salt in solution (e.g., phosphate buffered saline) injected into the joint. This is routinely determinable. Generally speaking, at a concentration of for example 5 mM, a dose of about 15-25 mL injected into knee joint or shoulder joint can be employed for DAB-4 linked nitroxide citrate salt, lower and higher amounts not being excluded, according to conventional considerations in humans. Knowing the in vitro image enhancing activity of DAB-4 linked nitroxide citrate salt per this invention and knowing the dose required to obtain satisfactory MRI contrast enhancement in a particular joint with, for example, Gd-DTPA, a person knowledgeable in MRI can readily predict the optimum dose for obtaining the desired degree of MRI contrast enhancement in a scan of that joint using DAB-4 linked nitroxide citrate salt.

Times between the end of injection and beginning of the MR image are especially advantageous for this invention. Typically, these are only 30-60 minutes. These reflect a preferred aspect of this invention where advantage is taken of the short times required for diffusion of DAB-4 linked nitroxide citrate salt into tissue sufficient for MRI image enhancement thereof. Such advantageous time differentials are preferably 30 minutes to 45 minutes. Of course, longer times are also within the scope of the invention.

Conventional MRI scanning techniques now employed extensively to obtain MR images of joints can be employed. See, e.g., DiChino, G., et al., Radiology 1985 157:373-377; Portugal, F. H., High Technology August, 1984, pp. 66-73: and Katzberg, R. W., "The Contrast Media Manual" (Williams and Wilkins, Baltimore, Md., 1992). Buckland-Wright C. Which radiographic techniques should we use for research and clinical practice? Best Pract Res Clin Rheumatol. February 2006; 20(1):39-55; Buckland-Wright J C, Macfarlane D G, Williams S A, Ward R J. Accuracy and precision of joint space width measurements in standard and macroradiographs of osteoarthritic knees. Ann Rheum Dis. November 1995; 54(11):872-880; Recht M P, Goodwin D W, Winalski C S, White L M. MRI of articular cartilage: revisiting current status and future directions. AJR Am J Roentgenol. October 2005; 185(4):899-914; Gold G E, Burstein D, Dardzinski B, Lang P. Boada F, Mosher T. MRI of articular cartilage in OA: novel pulse sequences and compositional/functional markers. Osteoarthritis Cartilage. 2006; 14 Suppl A:A76-86.

Without further elaboration, it is believed that one skilled in the art can, using the preceding description, utilize the present invention to its fullest extent. The following preferred specific embodiments are therefore to be construed as merely illustrative and not limitative of the remainder of the disclosure in any way whatsoever. Unless otherwise indicated, all parts and percentages are by weight. The entire disclosure of all applications, patents and publications cited herein are incorporated herein by reference.

EXAMPLE 1

Synthesis of DAB-4 Linked Nitroxide (Scheme 1)

In a solution of DMF (10 mL) containing DAB-4 (MW=316.5, 316 mg, 1 mmoles) was added N,N-diisopropylethylamine (DIEA, MW=129, d=0.78, 5.0 mmoles, 0.65 gm=0.83 mL) and 3-carboxy-2,2,5,5-tetramethyl-1-pyrrolidinyloxyl (MW=186, 5.0 mmoles, 0.93 gm) and the reaction was stirred at room temperature for ½ hr. Then, benzotriazole-1-yl-tris-(dimethylamino)phosphonium hexafluorophosphate, (BOP, MW=442, 5.0 mmoles, 2.21 gm) was added. This reaction was stirred overnight, about 16 hr, at room temperature. At that point, a sodium chloride solution (50 mL), sodium bicarbonate saturated (5 mL) and methylene chloride (100 mL) were added. The organic layer was separated, dried over anhydrous sodium sulfate and evaporated to dryness. The remaining residue was dried under high vacuum to remove remaining DMF. The resultant oil was chromatographed using silica gel (230-400 mesh, EMD Chemicals, distributed by VWR International, Bridgeport, N.J.). Elution with chloroform/acetone (40 mL/10 mL) brought down a small amount of a yellow compound, which was discarded. Changing to the following mixture: chloroform (25 mL)/methanol (25 mL) plus triethylamine (0.3 mL) afforded product one peak by TLC (silica gel, chloroform/methanol or alumina plates, chloroform/methanol). Mass spec (MW=989) confirms compound.

EXAMPLE 2

Synthesis of DAB-4 Linked Nitroxide (Scheme 1a)

In a solution of DMF (10 mL) containing DAB-4 (MW=316.5, 316 mg, 1 mmoles) was added 3-carboxy-2,2,5,5-tetramethyl-1-pyrrolidinyloxyl (MW=186, 5.0 mmoles, 0.93 gm) and O-(berizotrizol-yl)-N,N,N'N'-tetramethyluronim hexafluorophosphate (HBTU, MW=379, 1.9 gm, 5 mmoles). The reaction was stirred at room temperature for ½ hr. Then, N,N-diisopropylethylamine (DIEA, MW=129, d=0.78, 5.0 mmoles, 0.65 gm=0.83 mL) was added. This reaction was stirred overnight, about 16 hr, at room temperature. At that point, a sodium chloride solution (50 mL), sodium bicarbonate saturated (5 mL) and methylene chloride (100 mL) were added. The organic layer was separated, dried over anhydrous sodium sulfate and evaporated to dryness. The remaining residue was dried under high vacuum to remove remaining DMF. The resultant oil was chromatographed using silica gel (230-400 mesh, EMD Chemicals, distributed by VWR international, Bridgeport, N.J.). Elution with chloroform/acetone (40 mL/10 mL) brought down a small amount of a yellow compound, which was discarded. Changing to the following mixture: chloroform (25 mL)/methanol (25 mL) plus triethylamine (0.3 mL) afforded product one peak by TLC (silica gel, chloroform/methanol or alumina plates, chloroform/methanol). Mass spec (MW=989) confirms compound.

EXAMPLE 3

Synthesis of Citric Acid Salt of DAB-4 Linked Nitroxide (Schemes 1 and 1a)

Citric acid salt is prepared as follows. DAB-4-linked nitroxide (MW=989, 0.74 gm, 0.7 mmoles) prepared in Example 1 or 2, dissolved in dry $CHCl_3$, and citric acid anhydrous (MW=192, 0.14 gm, 0.7 mmoles dissolved in absolute ethanol are mixed together and evaporated to dryness. MW of citrate salt is 1,181.

EXAMPLE 4

Superiority of DAB-4 Linked Nitroxide Citrate for MRI Contrast of Cartilage

Comparison of DAB-4 linked nitroxide citrate and DAB-8 linked nitroxide citrate for enhancement of normal cartilage. Cylindrical immature bovine cartilage plugs were imaged by MR at 7 Tesla initially in saline and then in DAB-4 linked nitroxide citrate or DAB-8 linked nitroxide citrate. T1-weighted (T1W) images (TR=750 ms, TE=7 ms) and T1-value maps were performed. Images and T1 maps obtained ~30 minutes after immersion in the contrast agents are shown in FIG. 1. Diffusion of the contrast agent was restricted to occur only from the periphery and not from the top nor the bottom. The figures show:
a) DAB-8 linked nitroxide citrate
T1W image 27 min after immersion
b) DAB-4 linked nitroxide citrate
T1W image 29 min after immersion
c) DAB-8 linked nitroxide citrate
T1 value map 27 min after immersion
d) DAB-4 linked nistroxide citrate
T1 value map 29 min after immersion
e) For comparison, a pre-contrast T1 value map for the cartilage The DAB-8 linked nitroxide citrate shows much poorer penetration into the cartilage. The enhancement is difficult to detect on the T1W images. The T1 value maps show the T1 values drop (contrast penetration) for only a very thin rim of cartilage, only about ⅓ the distance for the DAB-4 linked nitroxide citrate.

EXAMPLE 5

Figure 1A:
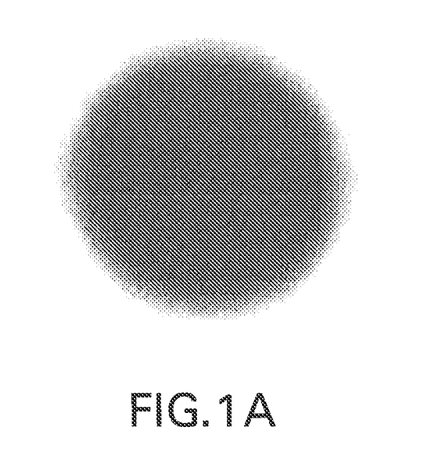
FIG. 1A: MRI T1W (weighted) image for DAB-8 linked nitroxide citrate was obtained at 27 minutes after immersion of normal cartilage in the contrast agent is shown.
Figure 1B:
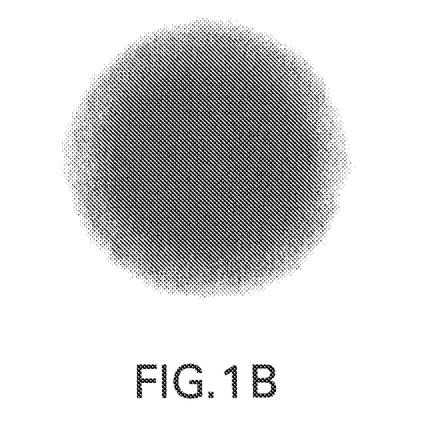
FIG. 1B: MRI T1W (weighted) image for DAB-4 linked nitroxide citrate was obtained at 29 minutes after immersion of normal cartilage in the contrast agent is shown.
Figure 1C:
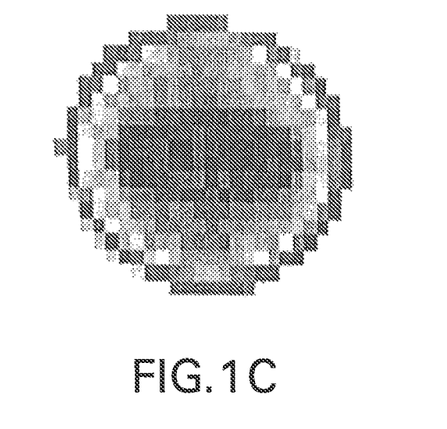
FIG. 1C: MRI T1 value map image for DAB-8 linked nitroxide citrate was obtained at 27 minutes after immersion of normal cartilage in the contrast agent is shown.
Figure 1D:
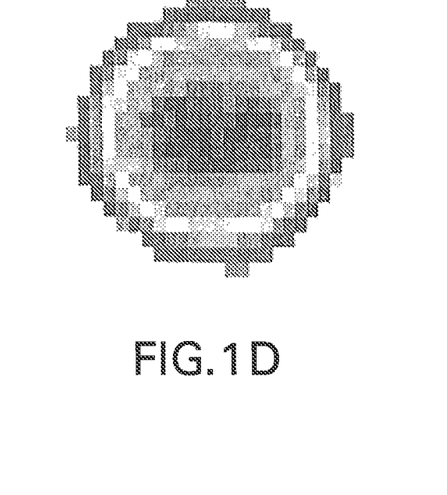
FIG. 1D: MRI T1 value map image for DAB-4 linked nitroxide citrate was obtained at 29 minutes after immersion of normal cartilage in the contrast agent is shown.
Figure 1E:
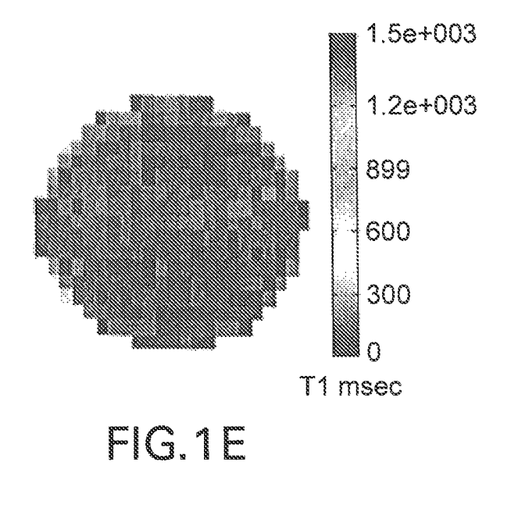
FIG. 1E: A pre-contrast T1 value map for normal cartilage is shown.
Figure 2A:
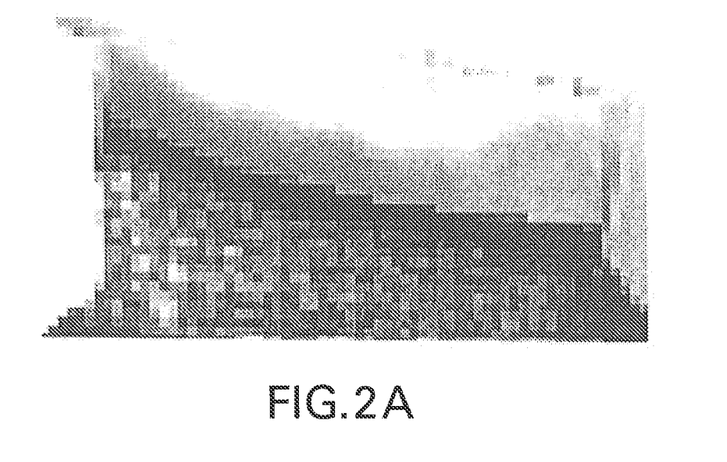
FIG. 2A: MRI Ti1 value map for DAB-4 linked nitroxide citrate in cartilage, indicating high levels of contrast media and more glycosaminoglycans (GAG) in the cartilage is shown.
Figure 2B:
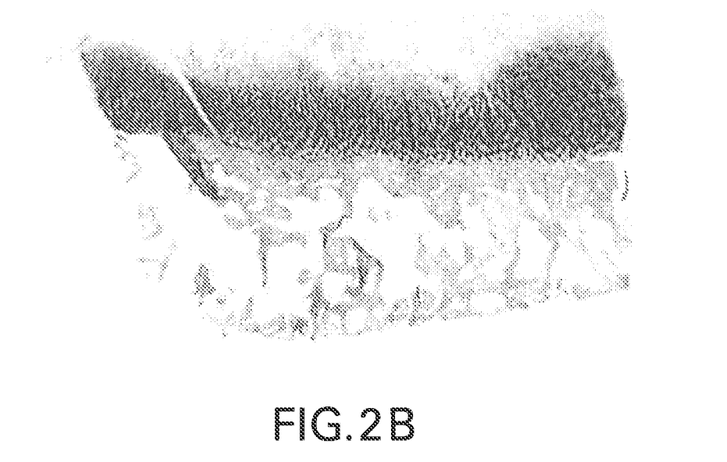
FIG. 2B: Histology of the same specimen stain with Saframin-O/fast Green is shown. Comparison of FIG. 2a) with FIG. 2b) shows high GAG concentration in the same areas as indicated by DAB-4 linked nitroxide on the T1 value map and the stain on the histology map.

Effectiveness of DAB-4 Linked Nitroxide Citrate to Enhance Contrast for Articular Cartilage Assessment as Measured by GAG Targeting Cartilage-bone plug excised from a human tibial plateau that was retrieved from total knee replacement surgery was equilibrated in DAB-4 linked nitroxide citrate. T1 value map (as acquired for FIG. 1) is compared to histology in FIG. 2:
a) T1 value map: orange color is lower T1 value indicating more contrast agent and more glycosaminoglycans (GAG) in the cartilage.
b) Histology of the same specimen stained with Safranin-O/fast green.
Comparison of FIG. 2*a*) with FIG. 2*b*) shows high GAG concentration in the same areas indicated by DAB-4 linked nitroxide on the T1 value map and the stain on the histology map.

EXAMPLE 6

Figure 3:
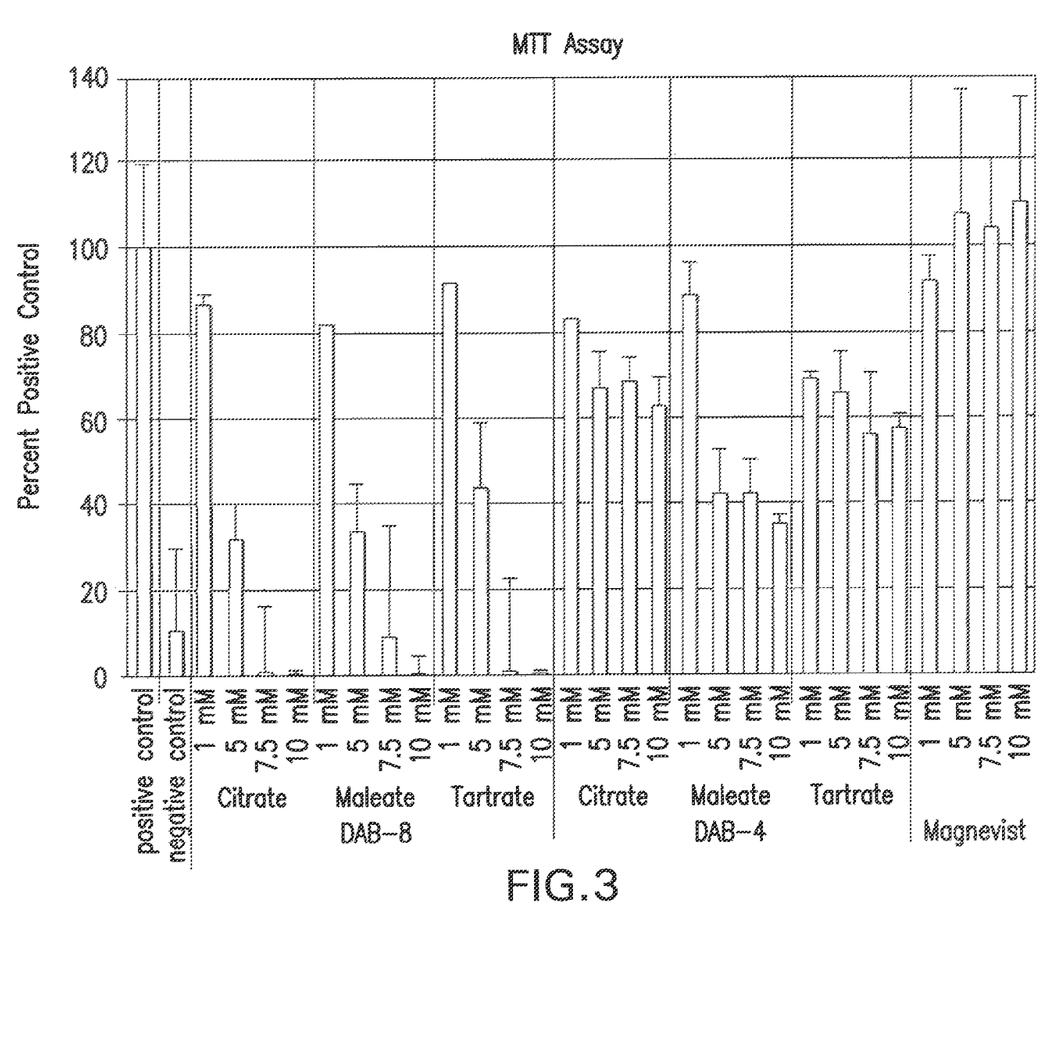
FIG. 3: Results for the MTT assay using the citrate, maleate and tartrate salts of DAB-4 linked nitroxide, DAB-8 linked nitroxide and Magnevist are shown.

Summary of Cytotoxicity Studies Comparing Salts of Dendrimer-Linked Nitroxides Based on DAB-4 and DAB-8 Dendrimer Cores with Magnevist and Positive and Negative Controls Assays: Modified MTT assay for metabolic activity (absorbance).
Quantitative picogreen for cell proliferation (μgDNA/ml).
Assay data analysis: Expressed as % of the positive controls for MTT and picogreen. MTT absorbance measures then normalized to the μgDNA/ml generated by the picogreen assay.
Cell cultures: RES-LTC chondrosarcoma cell line. Expresses hyaline-like chondrocyte phenotype and reliably produces large, homogeneous cell populations
Compounds Tested:
Positive control—culture medium only
Negative control—5 μM Staurosporine
Magnevist—1 mM, 5 mM, 7.5 mM, 10 mM
DAB-4 linked nitroxide Citrate—1 mM, 5 mM, 7.5 mM, 10 mM
DAB-4 linked nitroxide Maleate—1 mM, 5 mM, 7.5 mM, 10 mM
DAB-4 linked nitroxide Tartrate—1 mM, 5 mM, 7.5 mM, 10 mM
DAB-8 linked nitroxide Citrate—1 mM, 5 mM, 7.5 mM, 10 mM
DAB-8 linked nitroxide Maleate—1 mM, 5 mM, 7.5 mM, 10 mM
DAB-8 linked nitroxide Tartrate—1 mM, 5 mM, 7.5 mM, 10 mM
Methods:
Cell cultures in 96 well plates. Each compound, at a fixed concentration, was added in triplicate for each assay. MTT and picogreen assays in separate plates (assays interfere with each other). All plates treated together. Assays run at 48 hour timepoint. Microscopy performed to confirm findings.
Results for the MTT assay are shown in FIG. 3. At concentrations above 1 mM, DAB-8 linked nitroxide shows less metabolic activity than positive controls (untreated), or DAB-4 linked nitroxide and Magnevist. DAB-4 linked nitroxide showed less metabolic activity than positive controls but greater than for DAB-8 linked nitroxide. The citrate salt of DAB-4 linked nitroxide showed more metabolic activity than the maleate or tartrate salts.

Figure 4:
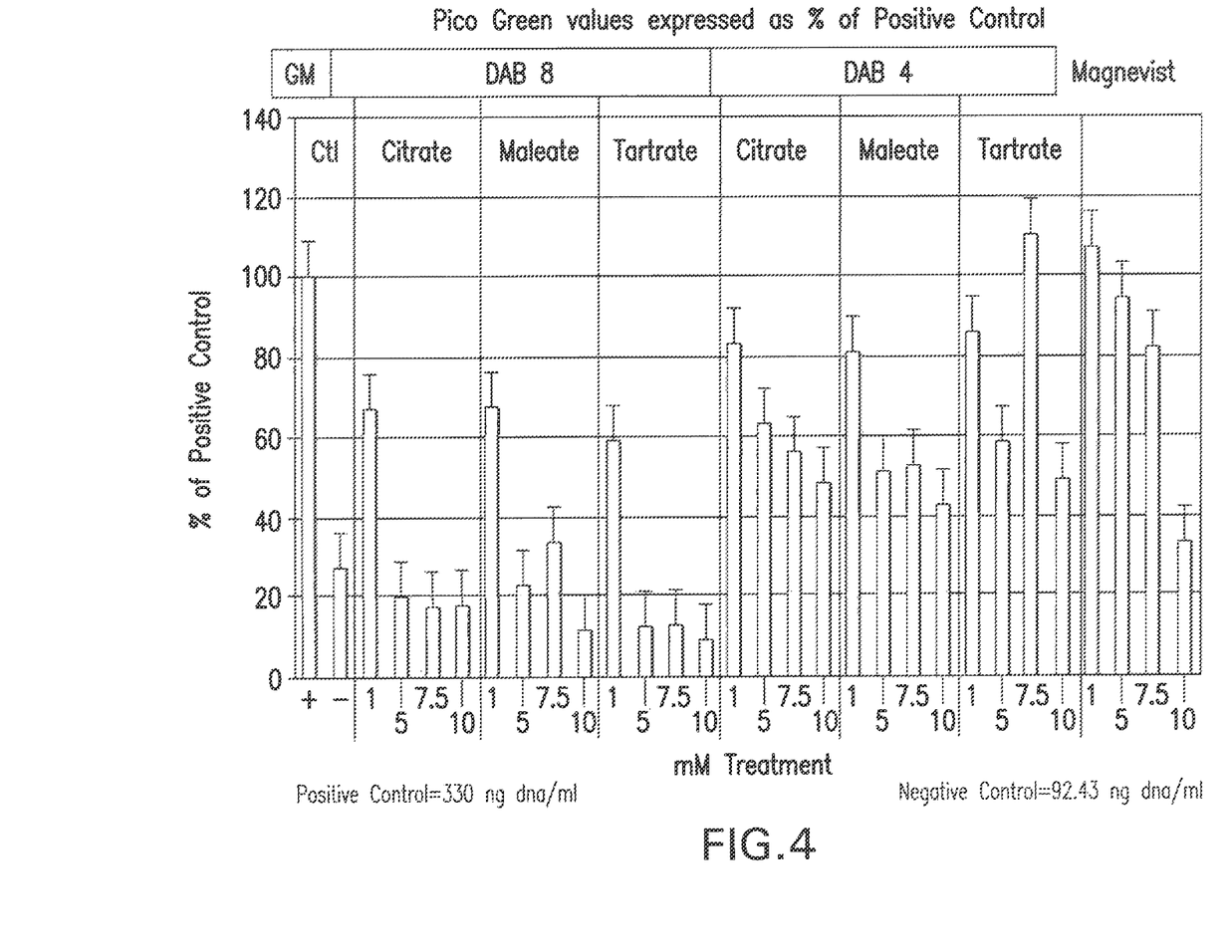
FIG. 4: Results for the Picogreen assay using the citrate, maleate and tartrate salts of DAB-4 linked nitroxide, DAB-8 linked nitroxide and Magnevist are shown.

Results for the Picogreen assay are shown in FIG. 4. DAB-8 linked nitroxide citrate shows lower cell proliferation than positive control, (untreated), DAB-4 linked nitroxide maleate and Magnevist at all concentrations. All DAB-4 linked nitroxide salts show a dose-dependent effect. The 7.5 mM DAB-4 linked nitroxide tartrate appears to be an outlier. Magnevist at 10 mM shows low cell proliferation. It is not clear if the lower cell proliferation is due to cell death or an initial delay in proliferation.

Figure 5:
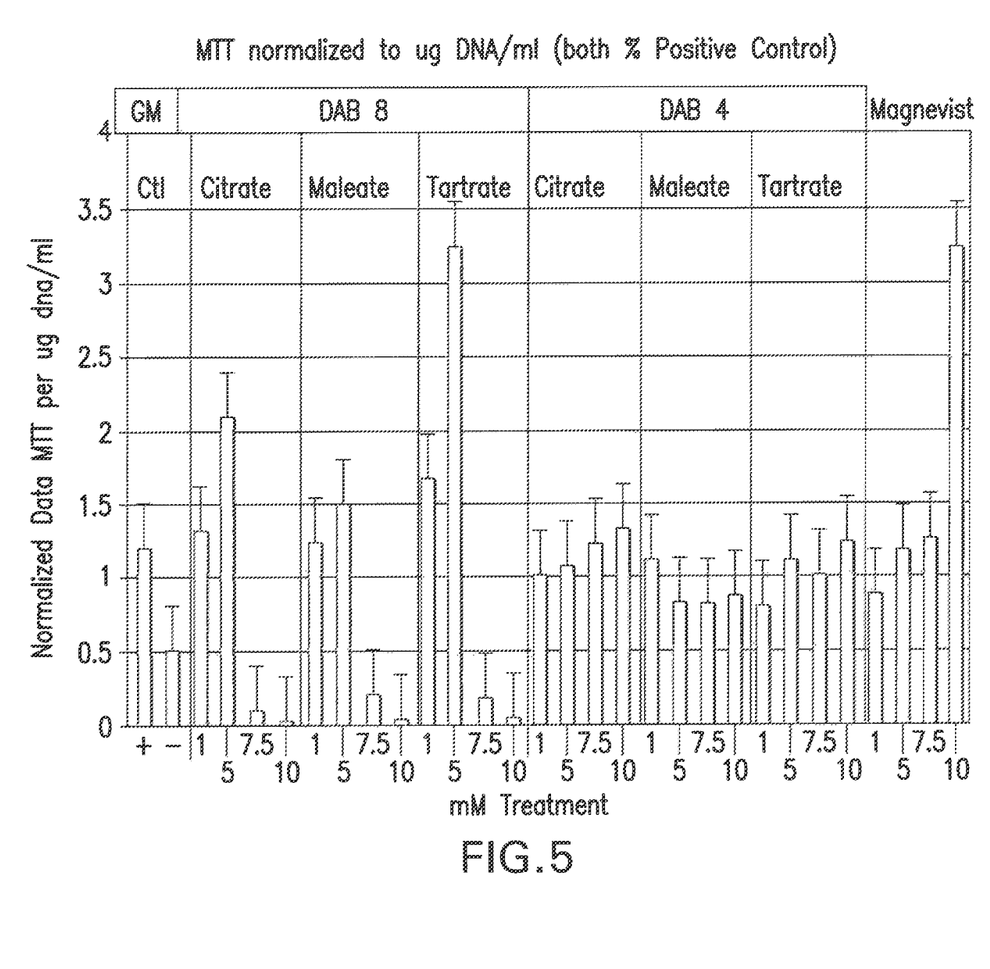
FIG. 5: Results for the MTT data normalized to gDNA/ml using the citrate, maleate and tartrate salts of DAB-4 linked nitroxide, DAB-8 linked nitroxide and Magnevist are shown.

Results for MTT data normalized to μgDNA/ml are shown in FIG. 5. This is a measure of the metabolic activity of the cells normalized to the concentration of cells (μgDNA/ml), i.e. the "health" of the cells. DAB-4 linked nitroxide salts perform similar to positive controls. DAB-8 linked nitroxide salts show effects above 1 mM. Magnevist appears abnormally high at 10 mM.

EXAMPLE 7

Toxicity Studies of DAB-4 Linked Nitroxide Citrate in Rabbit Joints

The potential inflammatory and structural effects of PBS, Magnevist, and DAB-4 linked nitroxide citrate were assessed using a single intra-articular injection model (data were taken from studies conducted by Arthroteq testing laboratory). Twelve female New Zealand White rabbits (2.7-3.3 kg) were randomly assigned to one of two study groups that received bilateral intra-articular injections with Magnevist (n=4) in the right stifle and sterile PBS in the left stifle, or DAB-4 linked nitroxide citrate (n=8, 0.3 mL of 10 mM) in the right stifle and sterile PBS in the left stifle (n=8, 0.3 mL).

Rabbits were euthanized two weeks post-injection. Both left and right stifles were harvested and immediately fixed in 10% neutral buffered formalin, then set for histological processing. Five-micron thick slides from each knee were stained with Hematoxylin & Eosin and Safranin-O.

Figure 6:
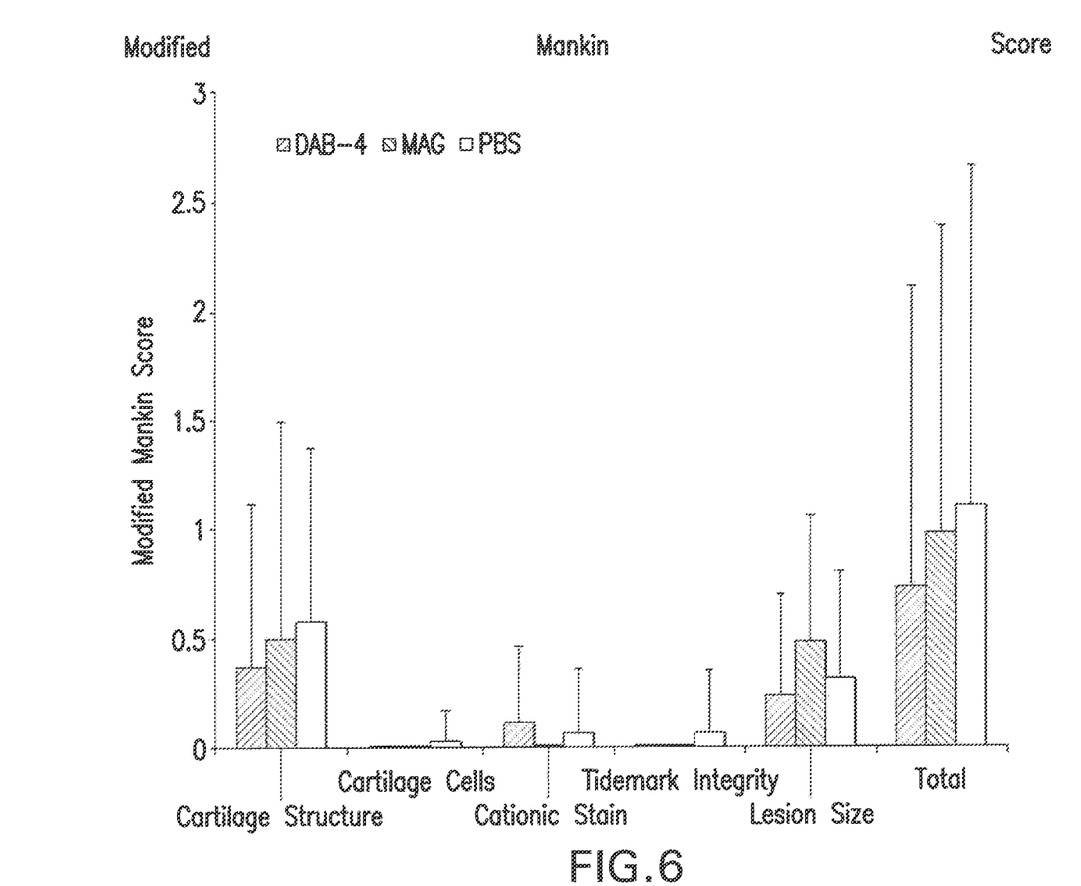
FIG. 6: Data from the Modified Mankin scores for join degeneration using DAB-4 linked nitroxide citrate, Magnevist and PBS, the latter two as controls is shown.

No animals presented clinical signs of inflammation or lameness during the study. Modified Mankin scoring did not uncover any signs of structural damage and/or degenerative response due to Magnevist, DAB-4 linked nitroxide citrate, or PBS injections (FIG. 6). Custom synovial inflammation scoring reflected the absent of an inflammatory response in all stifles and no difference between Magnevist or DAB-4 linked nitroxide and the PBS-injected stifles were observed (FIG. 7).

FIG. 6: No differences were detected in the Modified Mankin subscores or total score between any treatment groups as assessed by ANOVA. All tests were performed at a significance level of p<0.05. Mean cartilage degenerative changes assessed by Modified Mankin Scoring (Mean±S.D.) for all study groups. A higher score (maximum of 19) indicates greater joint degeneration. Mean subscores for a naïve group of age-matched rabbits normally fall in a range between 0 and 1.0. Total Mankin Score for a naïve group of age-matched rabbits normally falls in a range between 0 and 3.0.

Figure 7:
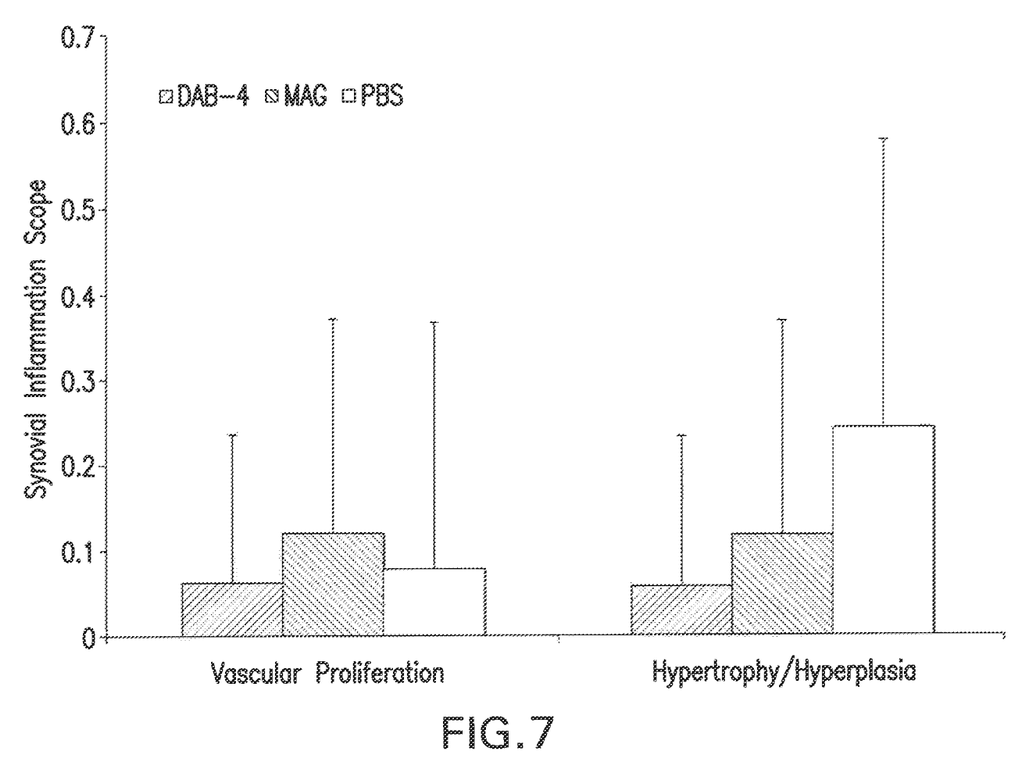
FIG. 7: Data from Synovial Inflammation scores for join degeneration using DAB-4 linked nitroxide citrate, Magnevist and PBS, the latter two as controls is shown.

FIG. 7: No differences were detected in the Synovial Inflammation subscores or total score between any treatment groups as assessed by ANOVA. All tests were performed at a significance level of p<0.05. Average scores (Mean±S.D.) for Synovial Inflammation for all study groups. A higher score indicates greater inflammation. Only two of the seven sub-categories presented non-zero scores. A mean score between 0 and 1.0 is typical for naïve age-matched rabbits.

EXAMPLE 8

MRI Images of a Knee Joint Using DAB-4 Linked Nitroxide Citrate

Figure 8:
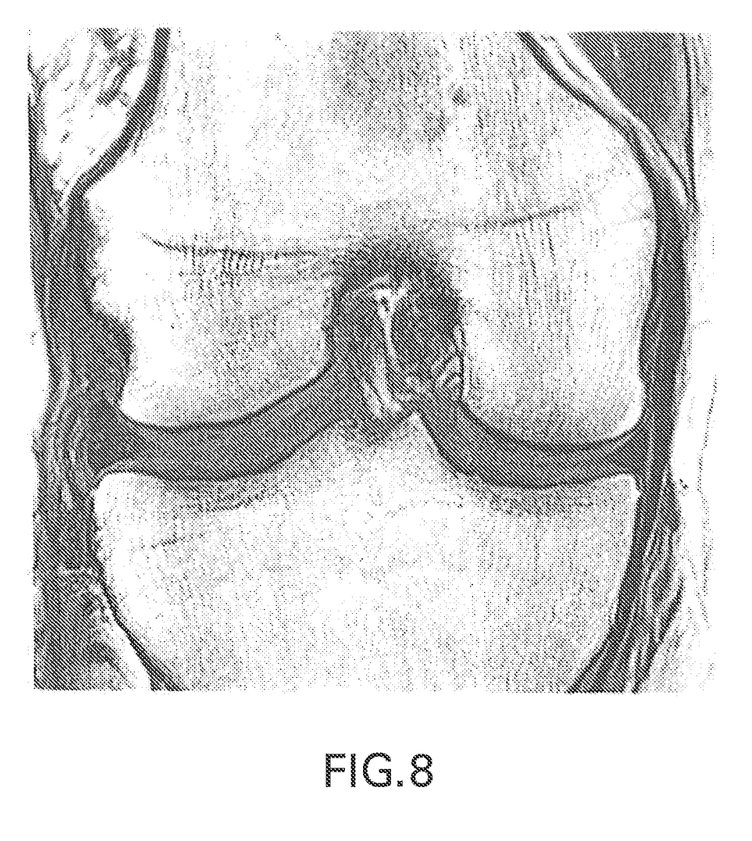
FIG. 8: T1-weighted MRI image of a control knee joint is shown.
Figure 9:
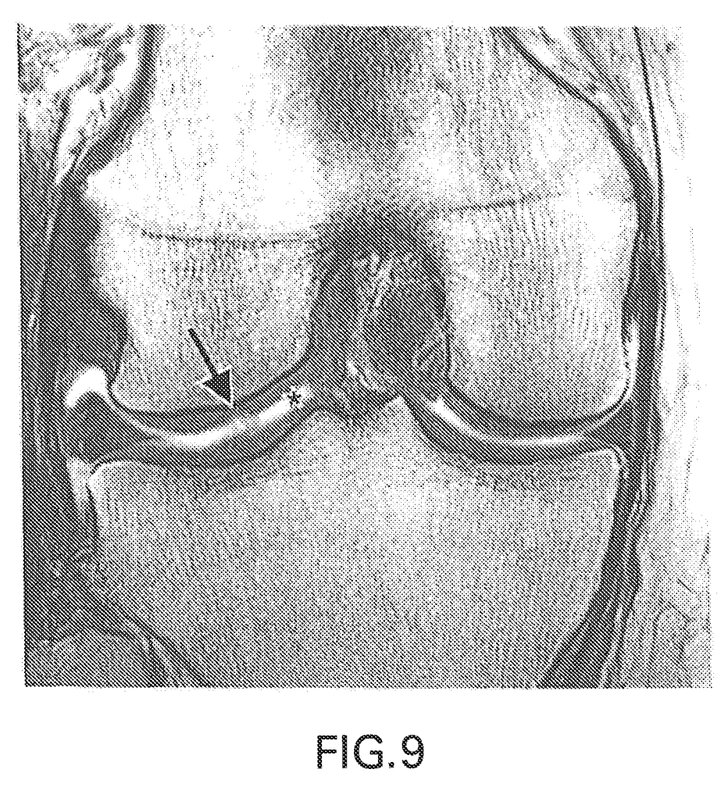
FIG. 9: T1-weighted MR image of a knee joint 10 minutes after intraarticular injection of DAB-linked nitroxide citrate is shown.

Coronal T1-weighted MR images of a human knee were taken in a human cadaver. The cartilage surfaces are poorly differentiated as shown in FIG. 8. Coronal T1-weighted MR contrast images were also taken ex vivo in a human cadaver 10 minutes after intraarticular injection of 25 ml of a 5 mM solution of DAB-4 citrate diluted in PBS. As shown in FIG. 9, the joint fluid (asterisk) is now bright and outlines the cartilage surfaces. A partial thickness cartilage defect (arrow) is easily identified. All images were performed on a Siemens Skyra 3 Tesla magnet using a 15 channel transmit/receive QED knee coil. (14 cm FOV (field of view); 3 mm thick slice; 384×384 matrix; TR 800 ms; TE 8.6 ms; Turbo factor of 2; receiver bandwidth 350 Hz/pixel.)

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method of imaging cartilage in a joint of a subject comprising: administering to the subject a citrate salt of diaminobutyl poly(propyleneimine) (DAB)-4 linked nitroxide and taking an magnetic resonance imaging (MRI) image of cartilage in the joint of the subject.

2. The method of claim 1 wherein the citrate salt is a 1:1 molar ratio citric acid:DAB-4 linked nitroxide.

3. The method of claim 1 wherein the image is taken 30-45 minutes after the DAB-4 linked nitroxide citrate is administered.

4. The method of claim 1 further comprising evaluating cartilage status of said joint.

5. A method of imaging a joint of a subject comprising:
   administering to the subject an amount of a citrate salt of DAB-4 linked nitroxide effective to enhance an MRI image of said joint and taking an MRI image of said joint.

6. The method of claim 5 wherein the citrate salt is a 1:1 molar ratio citric acid:DAB-4 linked nitroxide.

7. The method of claim 5 wherein the image is taken 30-45 minutes after the DAB-4 linked nitroxide citrate is administered.

8. The method of claim 5 further comprising evaluating cartilage status of said joint.

* * * * *